United States Patent [19]
Desiderio

[11] Patent Number: 5,682,912
[45] Date of Patent: Nov. 4, 1997

[54] ORAL HYGIENE AND LINGUAL STIMULATION DEVICE

[76] Inventor: Arnold J. Desiderio, 9777 Nickels Blvd., #707, Boynton Beach, Fla. 33436

[21] Appl. No.: 631,209

[22] Filed: Apr. 12, 1996

[51] Int. Cl.⁶ .................................................. A61C 15/00
[52] U.S. Cl. ................................... 132/329; 132/321
[58] Field of Search ............................. 132/321, 329; 433/141, 216

[56] References Cited

U.S. PATENT DOCUMENTS

| | | | |
|---|---|---|---|
| D. 221,079 | 7/1971 | Muhler | D24/1 |
| D. 238,907 | 2/1976 | Bengtsson | D86/10 D |
| D. 258,318 | 2/1981 | Bengtsson | D28/64 |
| D. 294,072 | 2/1988 | Stern et al. | D25/64 |
| D. 298,855 | 12/1988 | White | D24/11 |
| D. 309,039 | 7/1990 | Ljungberg . | |
| 3,605,765 | 9/1971 | Canby | 132/93 |
| 3,779,256 | 12/1973 | Maloney et al. | 132/329 |
| 3,802,445 | 4/1974 | Wesley | 132/321 |
| 4,271,854 | 6/1981 | Bengtsson | 132/329 |
| 4,583,564 | 4/1986 | Finkelstein et al. | 132/321 |
| 4,832,061 | 5/1989 | Hwang | 132/329 |
| 5,044,041 | 9/1991 | Ljungberg . | |
| 5,050,625 | 9/1991 | Siekmann | 132/329 |
| 5,076,301 | 12/1991 | Sulskis | 132/321 |
| 5,183,063 | 2/1993 | Ringle et al. | 132/329 |
| 5,293,886 | 3/1994 | Czapor | 132/329 |

*Primary Examiner*—Nicholas D. Lucchesi
*Attorney, Agent, or Firm*—Foley & Lardner

[57] ABSTRACT

An elongated, flexible, unitary oral hygiene and lingual stimulation device which has a handle portion at one end, an interdental and gingival margin cleaning portion at the opposite end; and an intermediate portion therebetween. The intermediate portion may be folded back on itself to form a loop when the ends of the device are brought together. The loop may be scraped gently over the surface of the tongue to remove dead cells, food debris and bacteria and to provide a pleasing and stimulating sensation for the user.

20 Claims, 1 Drawing Sheet

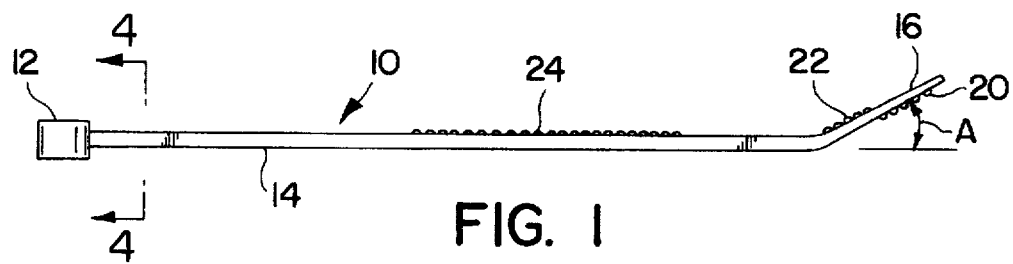
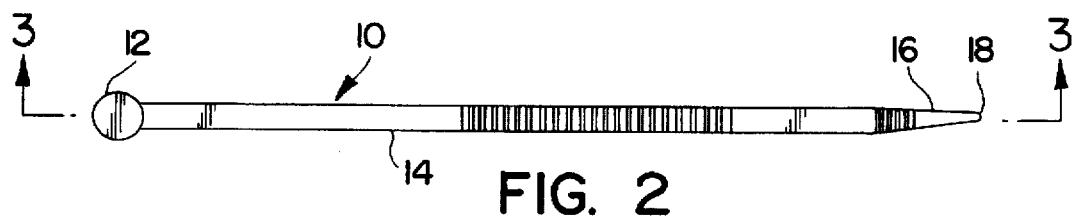
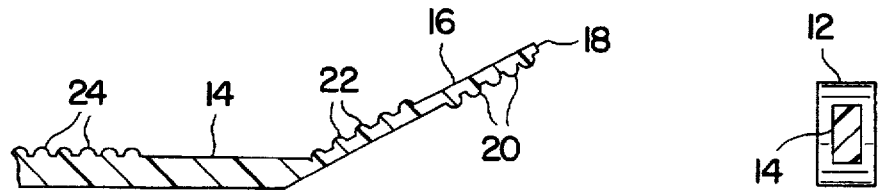 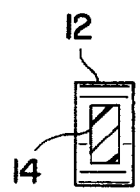
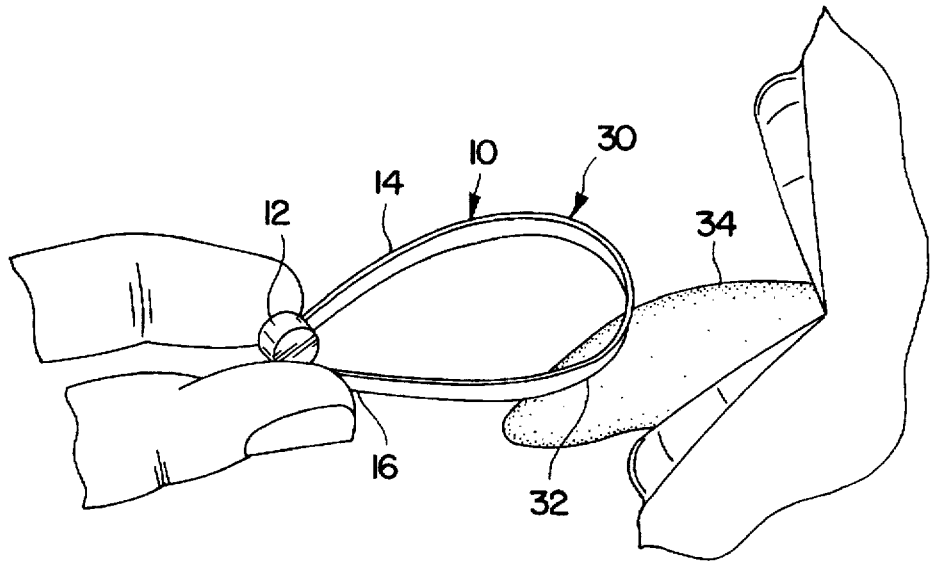

ORAL HYGIENE AND LINGUAL STIMULATION DEVICE

BACKGROUND OF THE INVENTION

1. Field of the Invention The present invention relates generally to oral hygiene devices and, more particularly, to such devices for cleaning interdental spaces, gingival margins, and tooth surfaces and for cleaning and stimulating the surface of the tongue and gum tissues.

2. Description of the Prior Art

Oral hygiene devices of many types have been widely used in the past. Such devices include toothbrushes, water irrigators, rubber gingival stimulators, dental floss, toothpicks and the like. Prior art toothpick devices are generally rigid, elongated structures, made of wood or plastic, having various shapes and configurations adapted primarily to clean the spaces between the teeth. Some prior art toothpick devices additionally provide roughened surface treatments or textures so that the gum tissues adjacent the interdental spaces are stimulated while the spaces are cleaned of food debris.

Exemplary of such prior art devices are those illustrated and described in U.S. Pat. Nos. 3,605,765 to Canby; 3,779,256 to Maloney et al.; 4,832,061 to Hwang; 5,076,301 to Sulskis; D221,079 to Muhler; D238,907 to Bengtsson; D258,318 to Bengtsson; D294,072 to Stern et al.; and D298,855 to White.

While each of the prior art devices described and referred to above have generally served their intended purpose, they have not proven to be entirely satisfactory since they have yet to fill the need for a simple, inexpensive, convenient device capable of performing all required functions of proper oral cleansing as well as providing for stimulation of gingival and lingual tissues in a comprehensive oral care program.

SUMMARY OF THE INVENTION

The present invention is summarized in that an elongated, flexible, unitary oral hygiene and lingual stimulation device has a handle portion disposed at one end, and interdental and gingival margin cleaning portion disposed at the opposite end, and an intermediate portion disposed therebetween, the intermediate portion being configured to be capable of being folded back on itself to form a loop when the ends of the device are brought together, the loop having a longitudinal edge adapted to remove dead cells, food debris and bacteria from the tongue and to stimulate tongue surfaces when the device is gently scraped over the surface thereof.

It is an object of the present invention to provide a convenient, daily oral hygiene instrument that can be used inconspicuously and effectively as part of a comprehensive program of dental care.

The present invention has a further object in providing effective cleaning of interdental spaces and gingival margins while at the same time facilitating the stimulation of gingival tissues and lingual surfaces.

The present invention is advantageous over the prior art in providing both cleaning of dental surfaces, interdental spaces, and gingival margins as well as stimulation of soft tissues of the tongue and gums.

Other objects and advantages of the present invention will become apparent from the following description of the preferred embodiment when taken in conjunction with the accompanying drawing.

BRIEF DESCRIPTION OF THE DRAWING

FIG. 1 is a side elevational view of a preferred embodiment of an oral hygiene and lingual stimulation device according to the present invention;

FIG. 2 is a top plan view of the embodiment of FIG. 1 according to the present invention;

FIG. 3 is an enlarged partial sectional view taken along line 3—3 of FIG. 2;

FIG. 4 is an enlarged sectional view taken along line 4—4 of FIG. 1; and

FIG. 5 is a perspective view of the embodiment of FIG. 1 in accordance with the present invention folded back to form a loop for stimulation of the surface of the tongue.

DESCRIPTION OF THE PREFERRED EMBODIMENT

The present invention is embodied in an elongated, unitary oral hygiene and lingual stimulation device 10 having a generally cylindrical handle portion 12 formed at one end thereof. Extending from the handle portion 12 is a main body portion 14. Body portion 14 is shaped in the form of an elongated ribbon of generally rectangular cross-section, as shown in FIG. 4.

At the distal end of main body member 14, a cleaning portion 16 is formed. The cleaning portion 16 is disposed with respect to the longitudinal direction of main body member 14 at an acute angle A as illustrated in FIG. 1. In a preferred embodiment, angle A is a 30° angle. As shown in FIG. 2, the cleaning portion 16 formed at the distal end of main body member 14 is tapered along its lateral edges to form a slightly narrowed, round tip 18.

Turning now to FIGS. 1 through 3, it can be seen that several sets of laterally oriented ridges are provided on the top and bottom surfaces, as visualized in FIG. 1, of the device 10. A first set of ridges 20 is formed on the bottom surface of the cleaning portion 16. On the top surface of cleaning portion 16, a second set of laterally extending ridges 22 is formed. As shown in FIGS. 1 and 3, the first and second sets of ridges 20 and 22, respectively, are longitudinally offset with respect to each other along the longer dimension of the device 10. A third set of ridges 24 is formed on the top surface of the main body portion 14, as shown in FIG. 1. Each of the ridges of sets 20, 22 and 24 have a generally semicircular cross-section, as best shown in FIG. 3. In a preferred embodiment, sets 20 and 22 comprise approximately five (5) ridges each and protrude approximately 0.005 inches from the surfaces on which they are located. Set 24 preferably consists of approximately 20 ridges, each having approximately the same dimension as those of sets 20 and 22.

In a preferred form, device 10 is integrally molded from synthetic material. Polyethylene has been found to be particularly satisfactory, and high density polyethylene is preferred. In terms of dimensions, handle portion 12 preferably has a diameter of approximately five (5) millimeters and a height, as visualized in FIG. 1, of approximately three (3) millimeters. The main body portion 14 is preferably one (1) millimeter by two and one-half (2½) millimeters in cross-section. The cleaning portion 16 has similar cross-sectional dimensions, tapering as illustrated in FIG. 2 to its rounded tip 18. Cleaning portion 16 may be somewhat thinner if it is desired to provide cleaning in smaller interdental spaces. The overall length of device 10 is preferably in the range of three (3) inches to four (4) inches, most suitably three and one-half (3½) inches.

By constructing device 10 in the dimensions specified and by integrally molding all portions of polyethylene, or high density polyethylene, the device may be used easily and conveniently for both cleaning and stimulation purposes. In a relaxed condition, the device 10 assumes the linear profile shown in FIGS. 1 and 2, thereby facilitating the cleaning of all interdental spaces and gingival margins. The length of the device is such that it may be used inconspicuously and conveniently. The device is sufficiently long as to facilitate the cleaning of all interdental spaces and margins, even those at the back of the mouth, without difficulty. At the same time, it is not so long as to be difficult to manipulate.

When it is desired to utilize the device 10 as a lingual stimulator, the main body portion 14 may be folded or bent back upon itself by bringing the handle portion 12 and the cleaning portion 16 together between the fingertips, as shown in FIG. 5. When device 10 is grasped in this manner, main body portion 14 forms a loop indicated generally at 30 in FIG. 5. The loop thus formed has an edge 32 which may be conveniently used to gently scrape off dead cells, food debris and bacteria from the surface 34 of the tongue. The use of device 10 in this manner not only accomplishes a desirable hygienic purpose but also provides for a pleasing, stimulating feeling for the user.

When the lingual stimulation procedure is complete, release by the user of end 16 allows the flexible, resilient main body portion 14 to return to its linear configuration, as shown in FIGS. 1 and 2. The memory inherent in the polyethylene material used for device 10 assures that it may be repeatedly deformed into a loop and released back to its linear form without damage and without diminishing any of its capabilities.

While device 10 may be re-used merely by taking appropriate sanitary precautions and cleansing the device between uses, it is sufficiently inexpensive to permit replacement as frequently as a user might desire.

Inasmuch as the present invention is subject to many variations, modifications and changes in detail, it is intended that all matter contained in the foregoing description or shown in the accompanying drawing shall be interpreted as illustrative and not in a limiting sense.

What is claimed is:

1. An elongated, flexible, unitary oral hygiene and lingual stimulation device comprising:
   a handle portion disposed at one end,
   an interdental and gingival margin cleaning portion disposed at the opposite end, and
   means for forming a loop comprising an intermediate portion disposed between said handle portion and said cleaning portion, said intermediate portion being movable between a generally elongated position wherein said interdental and gingival margin cleaning portion is generally linearly oriented with respect to said handle portion and a curvilinear position wherein said interdental and gingival margin cleaning portion contacts said handle portion to form said loop,
   said loop comprising, means for removing dead cells, food debris and bacteria from the tongue and for stimulating tongue surfaces when the device is gently scraped over the tongue.

2. The device as claimed in claim 1 formed of polyethylene.

3. The device as claimed in claim 1 formed of high density polyethylene.

4. The device as claimed in claim 1, wherein said cleaning portion is tapered.

5. The device as claimed in claim 4, wherein said tapered cleaning portion has a rounded end.

6. The device as claimed in claim 1, wherein said cleaning portion is provided with a set of spaced lateral ridges on one side thereof.

7. The device as claimed in claim 6, wherein said cleaning portion is provided with a second set of spaced lateral ridges on a side opposite said one side thereof, said sets of ridges being offset longitudinally with respect to each other.

8. The device as claimed in claim 1, wherein said intermediate portion is provided with a set of spaced lateral ridges on one side thereof.

9. The device of claim 8, wherein each of said ridges has a semicircular cross section.

10. The device as claimed in claim 9, wherein said intermediate portion is formed in a narrow ribbon having a length of between three (3) inches and four (4) inches.

11. The device as claimed in claim 1, wherein said device is generally rectangular in cross section.

12. The device as claimed in claim 1, wherein said handle portion is generally cylindrical, said cylindrical handle portion having an axis oriented orthogonally with respect to the longer dimension of said elongated device.

13. The device of claim 12, wherein said generally cylindrical handle portion has a diameter of approximately five (5) millimeters and a height of approximately three (3) millimeters.

14. The device as claimed in claim 1, wherein said cleaning portion is disposed at an angle relative to the longer dimension of said intermediate portion.

15. The device of claim 14, wherein said cleaning portion is disposed at an angle of approximately thirty degrees (30°) relative to the longer dimension of said intermediate portion.

16. The device as claimed in claim 1, wherein cross-sectional dimensions of said intermediate portion are approximately one (1) millimeter by two and one-half (2.5) millimeters.

17. A method of removing dead cells, food debris and bacteria from the tongue and for stimulating tongue surfaces comprising gently scraping said tongue surfaces with a longitudinal edge of a narrow, flexible strip which has been bent to form a loop.

18. The method of claim 17, further comprising forming said flexible strip of plastic.

19. The method of claim 17, further comprising forming a handle portion at an end of said strip.

20. The method of claim 19, wherein said strip is bent to form a loop by holding a distal end of said strip, which is opposite said handle portion, against said handle portion.

* * * * *